US005748748A

United States Patent [19]

Fischer et al.

[11] Patent Number: 5,748,748

[45] Date of Patent: May 5, 1998

[54] APPARATUS AND METHOD FOR INFLUENCING OSCILLATIONS IN THE PASSENGER COMPARTMENT OF A MOTOR VEHICLE AND APPARATUS AND METHOD FOR DETECTING DEFECTS IN A MOTOR VEHICLE

[75] Inventors: Matthias Fischer, Eltingshausen; Reinhard Feldhaus, Oerlenbach-Ebenhausen; Andreas Orlamünder, Schweinfurt, all of Germany

[73] Assignee: Fichtel & Sachs AG, Schweinfurt, Germany

[21] Appl. No.: 701,984

[22] Filed: Aug. 23, 1996

[30] Foreign Application Priority Data

Aug. 26, 1995 [DE] Germany ........................ 195 31 402.6

[51] Int. Cl.[6] ........................ A61F 11/06

[52] U.S. Cl. ........................ 381/71.4; 381/86

[58] Field of Search ........................ 381/71.1, 86, 94.1, 381/71.4, 71.3, 73.1

[56] References Cited

U.S. PATENT DOCUMENTS

| | | | |
|---|---|---|---|
| 3,071,752 | 1/1963 | Strasberg . | |
| 4,506,380 | 3/1985 | Matsui | 381/71 |
| 4,862,506 | 8/1989 | Landgarten et al. | 381/71 |
| 5,245,664 | 9/1993 | Kinoshite et al. . | |
| 5,267,310 | 11/1993 | Yoshiba | 381/71 |

FOREIGN PATENT DOCUMENTS

| | | |
|---|---|---|
| 0098594 | 1/1984 | European Pat. Off. . |
| 0415237 | 3/1991 | European Pat. Off. . |
| 0479367 | 4/1992 | European Pat. Off. . |
| 0559962 | 9/1993 | European Pat. Off. . |
| 0585875 | 3/1994 | European Pat. Off. . |
| 0671620 | 9/1995 | European Pat. Off. . |
| 2721754 | 11/1977 | Germany . |
| 3106029 | 9/1982 | Germany . |
| 4026070 | 2/1991 | Germany . |
| 4308398 | 9/1993 | Germany . |
| 4308923 | 9/1993 | Germany . |
| 1577322 | 10/1980 | United Kingdom . |
| 2228648 | 8/1990 | United Kingdom . |
| 2271908 | 4/1994 | United Kingdom . |
| 2273159 | 6/1994 | United Kingdom . |
| 9208225 | 5/1992 | WIPO . |

*Primary Examiner*—Curtis Kuntz
*Assistant Examiner*—Vivian Chang
*Attorney, Agent, or Firm*—Nils H. Ljungman and Associates

[57] ABSTRACT

An apparatus for modifying noise oscillations in a passenger compartment (12) of a motor vehicle (14) includes a memory device (38) for storing a plurality of predetermined oscillation patterns (SM), an operating condition determination device (18) for determining an operating condition (BZ) of the motor vehicle (14), a selector device (36) for selecting an oscillation pattern (SM) as a function of the determined operating condition (BZ) of the motor vehicle (14), and an oscillation generator device (39-42-44) for generating oscillations corresponding to the selected oscillation pattern (SM) into the passenger compartment (12) of the motor vehicle (14).

33 Claims, 7 Drawing Sheets

APPARATUS AND METHOD FOR INFLUENCING OSCILLATIONS IN THE PASSENGER COMPARTMENT OF A MOTOR VEHICLE AND APPARATUS AND METHOD FOR DETECTING DEFECTS IN A MOTOR VEHICLE

BACKGROUND OF THE INVENTION

1. Field of the Invention

The present invention relates to an apparatus for influencing oscillations in the passenger compartment of a motor vehicle.

2. Background Information

Such devices are used, for example, to reduce the noises transmitted from the source of the noise into the passenger compartment of a motor vehicle by transmitting a controlled secondary oscillation into the passenger compartment which is superimposed on the undesirable primary oscillation, and which, in the best case, neutralizes this primary oscillation by destructive interference.

German Patent No. 43 08 923 A1 relates to a device wherein a sensor located in proximity to the source of the noise can detect a reference signal, and utilizing a control unit, can calculate from this reference signal the oscillation pattern for a secondary oscillation utilized to neutralize the primary oscillation. The remaining noise following the superimposition of the primary oscillation and the secondary oscillation is detected by means of microphones located in the passenger compartment and is transmitted to the control device. On the basis of the frequency distribution of this residual noise, the coefficients used by the control unit to calculate the oscillation pattern of the secondary oscillation are defined so that they minimize the residual noise. The system disclosed in German Patent No. 43 08 923 A1, on the basis of the primary oscillation measured in the vicinity of the source of the noise and of the residual noise measured in the passenger compartment, therefore performs a control process to minimize the residual noise.

The computing effort required to perform the control process described in German Patent No. 43 08 923 A1 is very high, and the system reacts with a corresponding delay to any change in the primary oscillation emitted by the noise source. Moreover, on account of the control process, such systems also suppress primary oscillations from noise sources, in the vicinity of which there is no sensor to detect a corresponding reference signal. It can happen, for example, that such systems also at least partly neutralize noises which are either important for the driver in terms of maintaining his feel for the road handling characteristics of the vehicle and the characteristics of the road under the vehicle, e.g., tire noises, or sounds which the driver does not wish to have suppressed, as for example, music.

Of course, music is in general a rapid sequence of tones and cannot be altogether suppressed, on account of the slow reaction time of the control process, which is capable of neutralizing only quasi-stationary noises. But merely the attempt to suppress these noise sources can lead to the generation of a background noise which is subjectively unpleasant. Moreover, in a number of musical pieces, there are passages in which all of the instruments sustain tones for a long period of time, i.e., quasi-stationary tones, as for example in the introduction to "Also sprach Zarathustra" by Richard Strauss.

The systems described above respond to these passages and suppress the sustained notes, which has an adverse affect on the driver's enjoyment of the music.

OBJECT OF THE INVENTION

One object of the present invention is the provision of a device which is capable of influencing oscillations in the passenger compartment of a motor vehicle, which device is, on one hand, capable of reacting more rapidly to changing acoustical emissions, and on the other hand, suppresses only noises which are generated by actually unpleasant or undesirable sources of noise or vibrations.

SUMMARY OF THE INVENTION

The present invention teaches that this object can be accomplished by an apparatus to influence oscillations in a passenger compartment of a motor vehicle, which apparatus includes a memory device to store a plurality of predetermined oscillation patterns, an operating condition determination device to determine an operating condition of the vehicle, a selector device to select an oscillation pattern from the plurality of stored oscillation patterns as a function of the operating condition of the vehicle which has been determined, and an oscillation generator device to output oscillations which correspond to the selected oscillation pattern into the passenger compartment of the motor vehicle.

The present invention is based on the knowledge that not every operating condition of a motor vehicle is critical with regard to the generation of unpleasant noises, and that the operating conditions of the motor vehicle which are critical from the point of view of generating unpleasant noises can be correctly distinguished from operating conditions which are not critical from the point of view of generating unpleasant noises, by means of the signals provided by the sensor system which is conventionally present in the vehicle in any case, such as the sensor system for engine management. The invention therefore teaches that, at least for the operating conditions of the motor vehicle which are critical in terms of noise generation, oscillation patterns which are a function of the respective operating conditions are stored in a memory device. These oscillation patterns preferably cover essentially the entire frequency range of the type of oscillation in question. In the case of undesirable acoustical oscillations, this frequency range extends from approximately 20 Hz to approximately 20,000 Hz. The invention, however, can be used for physical vibrations which are transmitted via the vehicle body. The lower limit of this frequency range can be significantly below 20 Hz.

The selection device of the invention has access only to the oscillation patterns stored in the memory device, and from them selects the oscillation pattern which corresponds to the current operating condition of the vehicle. Finally, the oscillation pattern selected is converted by an oscillation generator into an oscillation which is transmitted into the passenger compartment of the vehicle.

The steps of detecting the operating condition and accessing the memory which must be performed to determine which oscillation pattern is required can be performed substantially incomparably more quickly than by the complex control process used in previously known systems. Since the acoustical pattern used for the secondary emission is also not determined on the basis of oscillation signals measured during operation of the vehicle, the oscillation pattern can be one which is designed to neutralize only certain noise sources which are present in the vehicle. For example, the oscillation pattern can be restricted to the suppression of the noises caused by the drive train of the vehicle, whereby noises which are caused, for example, by the interaction between the tires and the road or wind noises are not taken into consideration. The latter noises give the driver a feel for the characteristics of the road and for the speed of the vehicle, and are therefore generally very important for safe driving. Basically, however, it is also conceivable that the stored oscillation patterns could also take these noise sources into consideration.

German Patent No. 31 06 029 A1 relates to an apparatus for influencing oscillations in the passenger compartment of a motor vehicle in which an acoustical signal which corresponds to the speed of rotation of the internal combustion engine is emitted into the passenger compartment, whereby the frequency of the signal corresponds to a particularly unpleasant frequency. The phase and amplitude of the acoustical signal emitted are determined in a control process on the basis of a reference signal which is measured by a microphone located in the passenger compartment.

German Patent No. 40 26 070 A1 relates to an apparatus by means of which the microphones required to detect an acoustical signal in the passenger compartment can be installed in locations which are not close to the heads of the passengers. The described apparatus uses the real acoustical signals picked up by these microphones to derive a virtual acoustical signal which corresponds to a virtual microphone location in the immediate vicinity of the head of the passenger.

The system described in German Patent No. 27 21 754 A1 uses a stored advance signal as an initial wave form which is modified in a control circuit to minimize a residual acoustical signal picked up by a microphone. For the special case in which the primary sound to be suppressed has a constant wave form at a determined repetition rate which changes over time, such an advance signal for a defined frequency range is stored in a plurality of respective memories.

In GB 2 271 908 A, a Fourier transform of the primary oscillation detected is performed in a control circuit to determine the secondary oscillation to be transmitted into the passenger compartment, and following completion of the processing of the oscillation spectrum, a corresponding reverse transform is performed. The two transforms significantly increase the computer time and capacity required for the control system.

Although the apparatus according to the present invention for influencing vibrations in the passenger compartment of a motor vehicle is described above with reference to an example which relates to the suppression of abnormal or undesirable oscillations in the passenger compartment, it should be noted that the influence can also consist of changing an undesirable oscillation into a desirable oscillation as a function of the operating condition of the vehicle. For example, consideration can be given to changing the noises generated by the engine of a small car as heard in the passenger compartment into the noises generated by the engine of a sports car. Even physical vibrations of the vehicle body which are not actually present can be simulated for the driver. For example, a driver of a vehicle equipped with an automatic transmission or a continuously-shifting transmission sometimes can miss the sensation of a "jerk" which accompanies the change of gears. This jerk can now be simulated by using appropriate actuators. These actuators can be, for example, active seat bearings and/or transmission bearings and/or active differential bearings and/or active axle bearings.

By means of a tripping device which corresponds to the oscillation generator, it can be guaranteed by transmitting a tripping signal to the oscillation generator device that the oscillation which corresponds to the selected oscillation pattern will be transmitted in phase opposition to the primary oscillation which is acting on the passenger compartment. The tripping device thereby includes at least one oscillation sensor which is preferably located in the vicinity of the head of a passenger, in which case the tripping signal can be defined on the basis of the oscillations which are actually experienced by a passenger in the passenger compartment of a vehicle. As a result, it is possible in particular to prevent distortion or interference effects which can result if the oscillation sensor is located at a distance from the passenger compartment or from the passenger, on account of the transmission path between the location of the oscillation sensor and the passenger compartment or the passenger's head.

In one refinement of the tripping device, the present invention teaches that the tripping device includes a generator which generates an envelope family of curves to generate a predetermined envelope family of curves, the phase of which changes with respect to the primary oscillations as a function of the operating condition of the vehicle, as well as a tripping signal generator to output the tripping signal, when the envelope family of curves has completely overlapped the primary oscillation for a defined length of time. In this case, the defined length of time can be very short, e.g., only a few hundredths of a second, so that the overlapping of the primary oscillation by the envelope family of curves can be verified only over a few oscillation extremes (or peak values).

As noted above, the device for the determination of the operating condition can include the sensors which are conventionally provided for engine management. But the device can also advantageously include sensors, the output signals of which provide information on the load status of the vehicle, in particular how many persons are in it, and where they are sitting in the passenger compartment. In particular, the operating condition determination device can include an engine speed sensor to measure the speed of rotation of the engine of the vehicle and/or a speed sensor to measure the speed at which the motor vehicle is traveling, and/or a throttle valve sensor to measure the opening of a throttle valve of the engine of the vehicle and/or a gear sensor to detect the currently-engaged gear of the vehicle transmission and/or a longitudinal acceleration sensor to measure the longitudinal acceleration of the body of the vehicle and/or a lateral acceleration sensor to measure the lateral acceleration of the body of the vehicle and/or at least one load sensor to measure the load status of the vehicle.

So that it is also possible to inform a driver who has not yet become accustomed to the advantages of the apparatus according to the present invention to influence oscillations in the passenger compartment about a potential problem or malfunction of the apparatus according to the present invention, the apparatus can also include a monitoring device which monitors its correct operation, and if desired, a display device which corresponds to the monitoring device, which display device, when an abnormality or malfunction is detected by the monitoring device, indicates the existence of the abnormality or the malfunction to the user.

The spectrum of the primary oscillation transmitted from a source and acting on the passenger compartment changes over time, on account of wear and aging of the components of the vehicle which define the transmission path between the source and the passenger compartment. Consequently, the oscillation patterns which are required to suppress these primary oscillations may be different for an older vehicle than for a new vehicle. To adapt the oscillation patterns to the age or wear of the vehicle, in one refinement of the present invention, the present invention includes an interface which can be connected to a tuning device to define the oscillation patterns to be stored in the memory device as a function of predetermined operating conditions of the vehicle. The tuning device, for example, can be connected via the interface to the device claimed by the present invention during the regular inspections of the vehicle, and oscillation patterns which correspond to the respective age and wear of the vehicle can be transmitted to the memory device.

Basically, the tuning device can be formed simply by an external memory device which transmits predetermined oscillation patterns which correspond to the respective age and wear of the vehicle to the memory device of the apparatus claimed by the invention. An individual influence of the oscillations in the passenger compartment, and therefore one which is effective over a longer period of time, can be achieved if the tuning device includes an oscillation sensor which is located in the passenger compartment to measure the total oscillation which corresponds to the superimposition of the primary oscillation and the oscillation pattern selected, and an optimization device for the frequency-specific modification of the oscillation pattern.

In this case, the optimization device can preferably include at least one comparator which compares the amplitude of the resultant oscillation measured, as a function of the oscillation frequency, to a frequency-dependent threshold value. The comparator transmits a corresponding comparator signal to an oscillation pattern modification device, which functions in the manner of a synthesizer, for example, to modify the oscillation pattern to minimize the amplitude of the resultant oscillation measured as a function of the comparator signal.

As mentioned above, the oscillations can be acoustical oscillations, in which case loudspeakers are preferably used as the oscillation generator device and microphones as the oscillation sensors. Since modern vehicles are generally equipped with an audio system, in particular a stereo tape player and/or radio and/or CD players one refinement of the present invention teaches that the secondary acoustical oscillation is transmitted at least to the loudspeakers, and if possible, also to the output stage of this audio system.

To prevent distortion or interference effects which have a disadvantageous effect on the result of the whole process of influencing the oscillations, the present invention also teaches that the microphones are preferably located near an area in which the passengers' ears are located, at least when the vehicle is in motion. As a result, it becomes simple to minimize the length of the transmission path between the head of a passenger, in particular the head of the driver, and the location in which the microphones are installed. As mentioned above, the invention can also be used with oscillations which are transmitted as acoustic vibrations from the source of the oscillation into the passenger compartment and to the passengers.

In an additional aspect, the present invention further relates to a method for influencing oscillations in the passenger compartment of a motor vehicle. With regard to the variant embodiments of this method and their respective advantages, reference is made to the description of the apparatus according to the present invention presented above.

In an additional aspect, the present invention further relates to an apparatus for the detection of defects on a motor vehicle, having a memory device to store a plurality of predetermined oscillation patterns, an operating condition determination device to determine the operating condition of the motor vehicle, an oscillation sensor to detect oscillations in a passenger compartment of the vehicle and a comparator device to compare the oscillation pattern of the oscillations detected in the passenger compartment to an oscillation pattern stored in the memory device which corresponds to the determined operating condition of the vehicle, and to output a signal which indicates any deviations of the two oscillation patterns from one another. As mentioned above, age and wear of the components of the vehicle result in a change in the frequency spectrum of the primary oscillation emitted by the oscillation source. It is readily apparent that defects will also cause corresponding changes in the oscillation spectrum. The following portion of the description refers to a simple example to explain the effect of such a defect on the primary oscillation spectrum as well as one way to detect and analyze this defect.

Let us assume, for example, that a certain component in question makes a contribution to the primary oscillation spectrum as a result of resonance effects, which is therefore concentrated essentially in the natural frequency of the component in question. If this component contains a defect, its natural frequency changes, and the frequency spectrum of its contribution to the primary oscillation spectrum is shifted. Since the oscillation pattern stored in the memory device has been tuned for the non-defective vehicle, at two points in the resultant oscillation measured by the oscillation sensor in the passenger compartment there will be signal peaks, namely at the natural frequency of the non-defective component (this contribution is caused by the secondary oscillation emitted in the passenger compartment and corresponding to the stored oscillation pattern), and at the natural frequency of the defective component (this contribution results from the primary vibration acting on the passenger compartment and originating from the oscillation source).

These two oscillation contributions which are present in the resultant signal can be detected by the comparator device and can be displayed in the form of a signal which indicates the deviations of the two oscillation patterns from one another. From the frequency of the oscillation contribution which corresponds to the non-defective component, a conclusion can be reached as to which component is defective, and from the difference between the frequencies of the two oscillation contributions, a conclusion can be reached as to the type of defect, e.g., broken teeth in the transmission, wear in the drive train etc.

To make possible a defect detection device which is not adversely affected by noise, the present invention teaches that the comparator device includes a filter device which allows only those components of the signal indicating the deviations of the two oscillation patterns from one another to pass, the signal intensity of which is above a predetermined threshold value.

To facilitate the work of the repair personnel, the present invention also teaches that the apparatus includes an additional memory device to store the signals indicating the deviations of the two oscillation patterns from one another.

The present invention finally also relates to a method for detecting defects on a motor vehicle. With regard to the variant embodiments of this method and their advantages, reference is made to the preceding description of the apparatus for the detection of defects.

The above discussed embodiments of the present invention will be described further hereinbelow with reference to the accompanying figures. When the word "invention" is used in this specification, the word "invention" includes "inventions", that is, the plural of "invention". By stating "invention", the Applicant(s) does/do not in any way admit that the present application does not include more than one patentably and non-obviously distinct invention, and maintains that this application may include more than one patentably and non-obviously distinct invention. The Applicant (s) hereby assert(s) that the disclosure of this application may include more than one invention, and, in the event that there is more than one invention, that these inventions may be patentable and non-obvious one with respect to the other.

BRIEF DESCRIPTION OF THE DRAWINGS

The invention is explained in greater detail below with reference to the several embodiments which are illustrated in the accompanying figures.

DESCRIPTION OF THE PREFERRED EMBODIMENT

Figure 1:
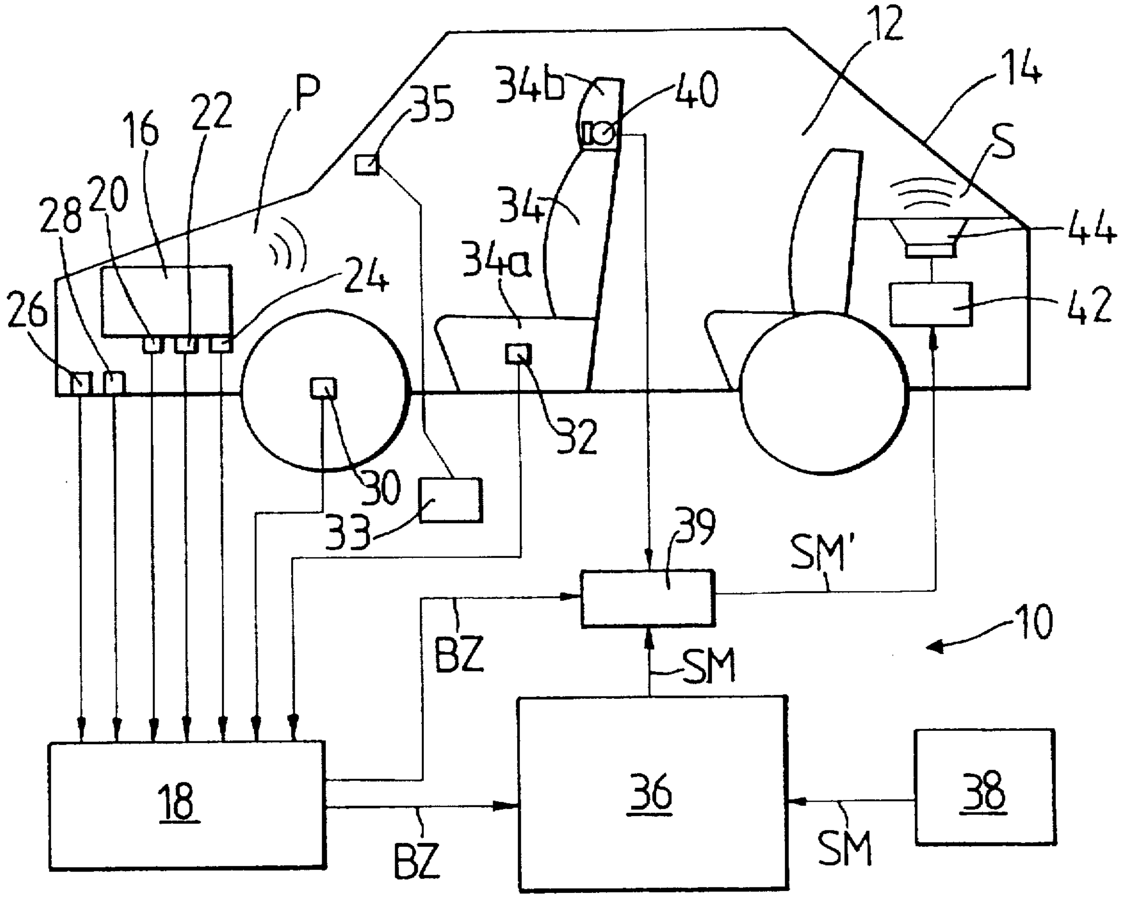
FIG. 1 is a schematic illustration of a motor vehicle which is equipped with a first embodiment of an apparatus as claimed by the invention to influence acoustical oscillations.

FIG. 1 shows an apparatus, designated 10 in general, which influences acoustic oscillations in the passenger compartment 12 of a motor vehicle 14. The term "acoustical oscillations" as used here refers to oscillations which are transmitted through the air and are audible to the unaided human ear, the frequencies of which are conventionally in a range of approximately 20 Hz to approximately 20,000 Hz. During operation of the motor vehicle 14, noises can be heard in the passenger compartment 12 which are caused, for example, by the drive train of the vehicle 14. To represent the engine, transmission, differential and the rest of the drive train, FIG. 1 shows the internal combustion engine 16 of the motor vehicle 14 as the source for the primary oscillations P experienced in the passenger compartment 12.

An operating condition determination unit 18 preferably uses a plurality of sensors to determine the current operating condition of the motor vehicle 14 at any desired point in time. These sensors can include a speed sensor 20 to measure the speed of the internal combustion engine 16, a throttle valve opening sensor 22 to measure the load on the internal combustion engine 16, a gear sensor 24 to identify the currently-engaged gear of a transmission on the vehicle 14, longitudinal acceleration sensors 26 (only one of which is shown in FIG. 1), lateral acceleration sensors 28 (only one of which is also shown in FIG. 1) to measure the longitudinal and lateral accelerations exerted on the vehicle body 14, a vehicle speed sensor 30 to measure the speed at which the vehicle is moving, as well as load sensors 32 to measure the load status of the vehicle 14.

The load sensors 32 can include pressure sensors installed in the seat cushions 34*a* of vehicle seats 34, like those which are already used in motor vehicles, for example, to inform a passenger who has just sat down in one of the seats 34 of the vehicle 14 to fasten the safety belt. Other load sensors which can be used include distance sensors (not shown), in particular those located in the vicinity of the rear axle, which can measure the change in length of a rear axle shock absorber as a result of the load placed in the trunk.

The operating status detection unit 18 emits an operating condition signal BZ which is formed from the output signals of the sensors 20–32 to a selector device 36. The selector device 36 is also connected to a memory device 38 in which oscillation patterns SM are stored at least for operating conditions BZ which are critical in terms of acoustical oscillations. An oscillation pattern SM(BZ)—that is, an individual oscillating pattern SM selected as a function of the detected operating condition BZ—which corresponds to the operating condition BZ is loaded by the selector device 36 from the memory device 38 and is used to suppress the primary oscillation P(BZ) in the passenger compartment emitted by the oscillation source 16 in this operating condition BZ.

So that the primary oscillation P can be effectively suppressed, it is necessary to emit a secondary vibration S generated from the oscillation pattern SM in phase opposition to the primary oscillation P into the passenger compartment 12. To guarantee the phase opposition, the selector device 36 supplies the oscillation pattern SM to a tripping (or energizing) device 39, the function of which is explained in greater detail with reference to FIG. 2.

Figure 2:
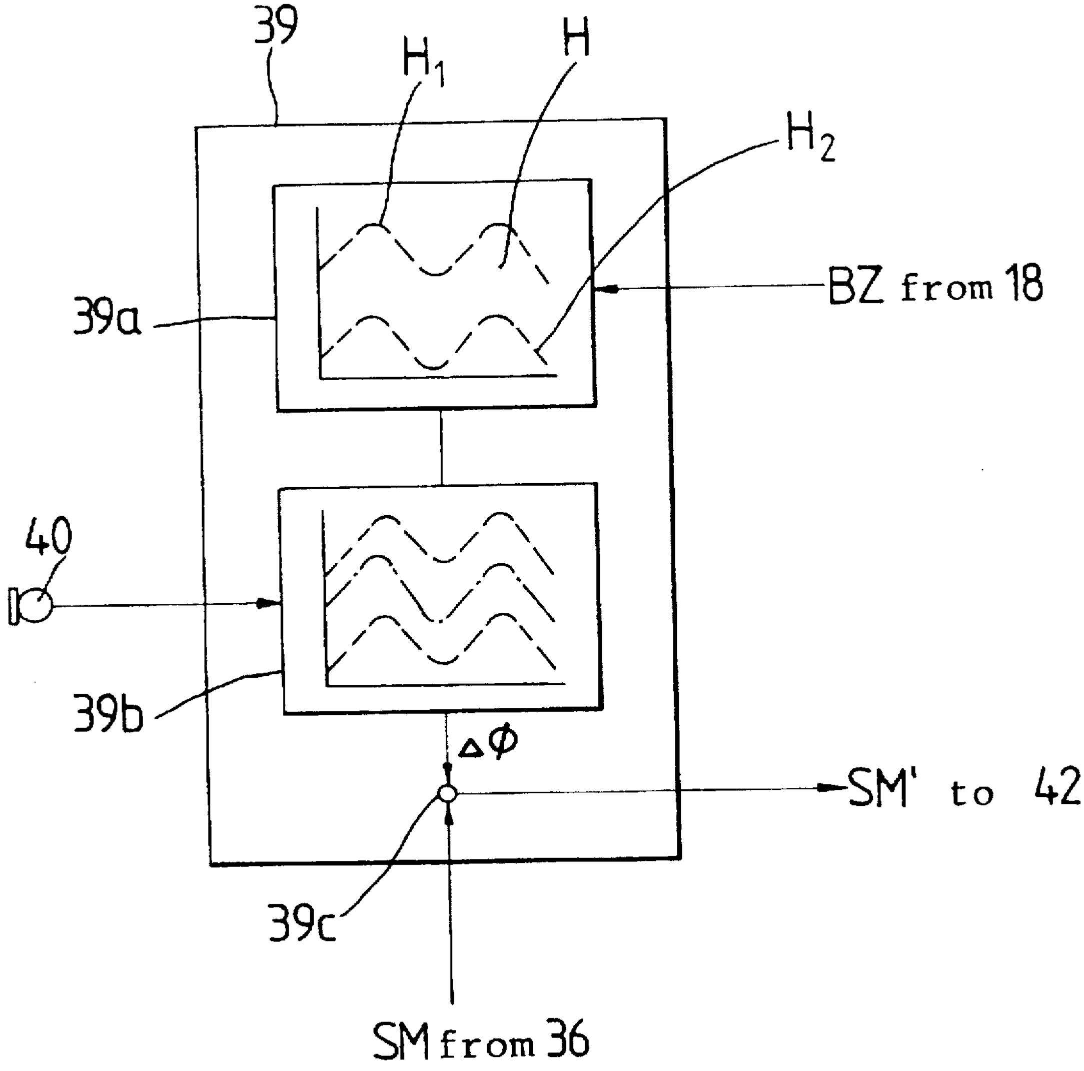
FIG. 2 is a schematic diagram illustrating the operation of the tripping device.

The tripping device 39 includes an envelope curve generator 39*a*, which generates an envelope family of curves H as a function of the operating condition signal BZ sent to it from the operating condition detection unit 18, which envelope family of curves H covers the area between the extreme envelope curves H1 and H2 illustrated in broken lines in FIG. 2. The tripping (or energizing) device 39 also includes a tripping signal generator 39*b* which compares the envelope family of curves H supplied to it by the envelope curve generator 39*a* to an oscillation signal (shown in dotted-dashed lines in FIG. 2) fed to it from a microphone 40 located in the passenger compartment 12, to determine whether this oscillation signal detected by the microphone 40 has been completely covered (or overlapped or cancelled) by the envelope family of curves H for a predetermined length of time. This length of time thereby corresponds to the chronological sequence of several oscillation peaks of the oscillations detected by the microphone 40 and is on the order of magnitude of several hundredths of a second.

To achieve complete overlap, the tripping signal generator 39*b* shifts the phase of the envelope family of curves H relative to the oscillation signal detected. If the overlap condition is fulfilled for the determined period of time, the tripping signal generator emits a tripping signal which indicates the defined phase shift $\Delta\Phi$ to a phase shifter 39*c*, which receives the oscillation pattern SM from the selector device 36 and forms a phase-shifted oscillation pattern SM'. The phase-shifted oscillation pattern SM' is transmitted to an output stage 42, which transmits it for output as secondary oscillations S into the passenger compartment 12 to a loudspeaker 44.

The microphone 40 which is part of the tripping device 39 is preferably located in the headrests 34b of the driver's seat 34. On account of the minimal distance between the driver's ears and the microphone 40, it can be substantially assured that the microphone "hears" practically the same thing as the driver, and in particular does not require a very long transmission path between the location of the driver's ears and the location of the microphone, which could cause distortion effects, interference effects, etc. In place of the one microphone 40, there can also be a plurality of microphones, which can be located as necessary in all the headrests of the front and rear seats of the vehicle 14.

If there is already an audio system in the vehicle 14, such as a stereo system with a radio receiver and a cassette or CD player, the apparatus claimed by the present invention can make use of the output stage or the output stages and the loudspeaker or the loudspeakers of this audio system, as a result of which the costs for the apparatus claimed by the present invention can be reduced accordingly.

It should also be added that the apparatus 10 can also include a monitoring device 33 which continuously or at regular intervals monitors the correct operation of its individual components, and emits a corresponding acoustical and/or optical signal to a display unit 35 when it detects an abnormality. The connections between the monitoring device 33 and these components which are necessary to monitor the individual components are not shown in FIG. 1 for purposes of simplification.

It should also be noted that although the apparatus claimed by the present invention has been described above primarily on the basis of the example of the suppression of primary oscillations P originating from the oscillation source 16, it is also possible not to suppress these primary oscillations P by means of the secondary oscillations S generated from the stored oscillation patterns SM, but to modify them in a controlled and desired manner. For example, consideration could be given to modifying the engine noises P of a compact car by the controlled superimposition of suitable secondary oscillations S, so that in the passenger compartment 12, the impression is given that the small car is actually a sports car.

Figure 3:
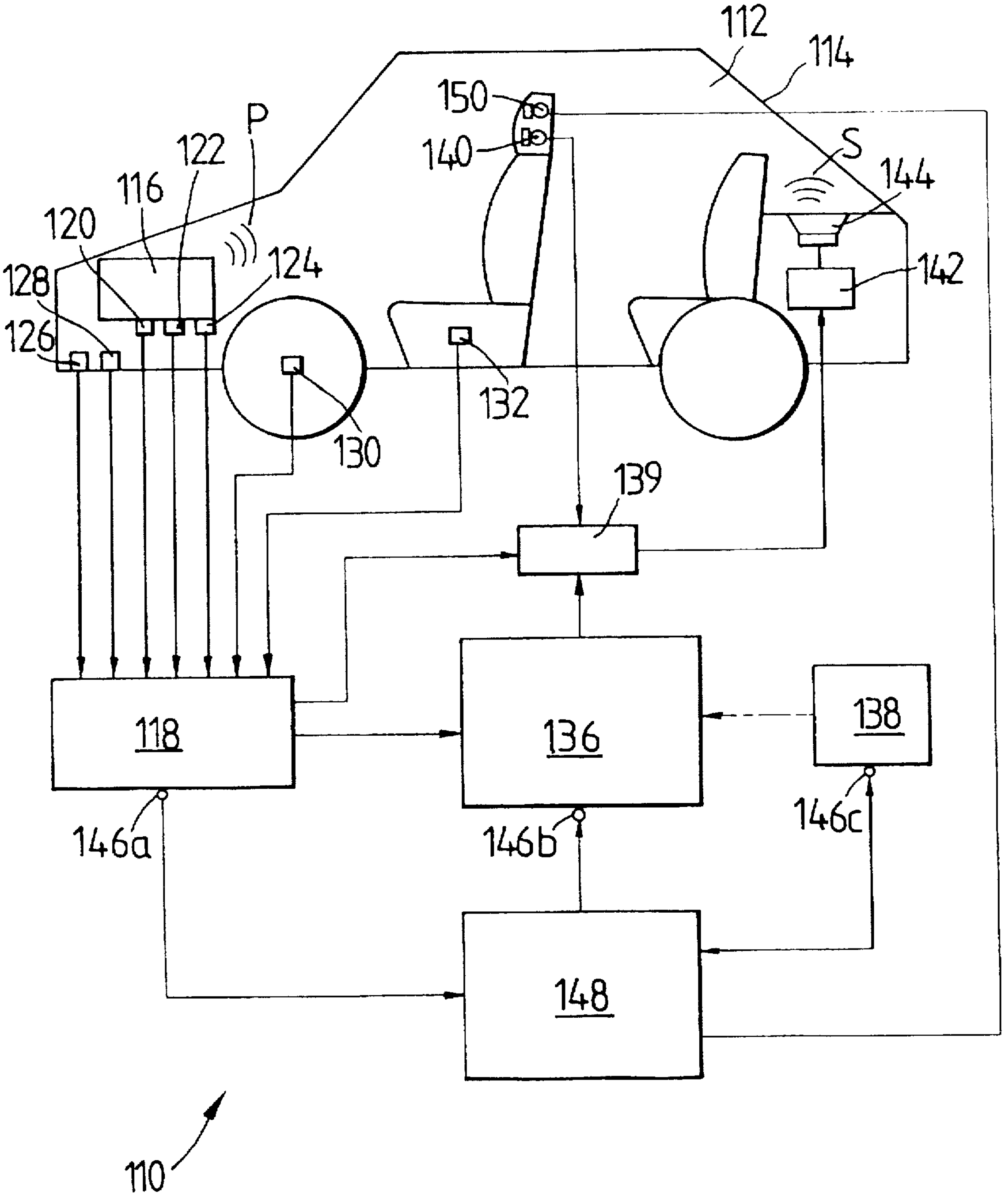
FIG. 3 is a schematic view similar to that of FIG. 1, but where a tuning device is connected to the apparatus claimed by the invention.

FIG. 3 illustrates a second embodiment of the apparatus according to the present invention which can be used to influence oscillations in the passenger compartment of a vehicle, which embodiment is essentially the same as the embodiment illustrated in FIG. 1. FIG. 3 therefore shows analogous parts with the same reference numbers as in FIG. 1, but plus 100. The embodiment illustrated in FIG. 3 is described below only to the extent that it differs from the embodiment illustrated in FIG. 1, and reference is hereby made expressly to the description which accompanies FIG. 1.

The apparatus 110 differs from the apparatus illustrated in FIG. 1 in particular because the operating condition determination unit 118, the selector device 136 and the memory device 138 are provided with respective interfaces 146a, 146b and 146c which are used for the connection of a tuning device 148. This tuning device 148 can be connected, for example, during the regular inspections of the vehicle 114, to the device 110, to adjust the oscillation patterns SM which are stored in the memory device 138 so that they correspond to the current age and wear of the vehicle 114.

Figure 4:
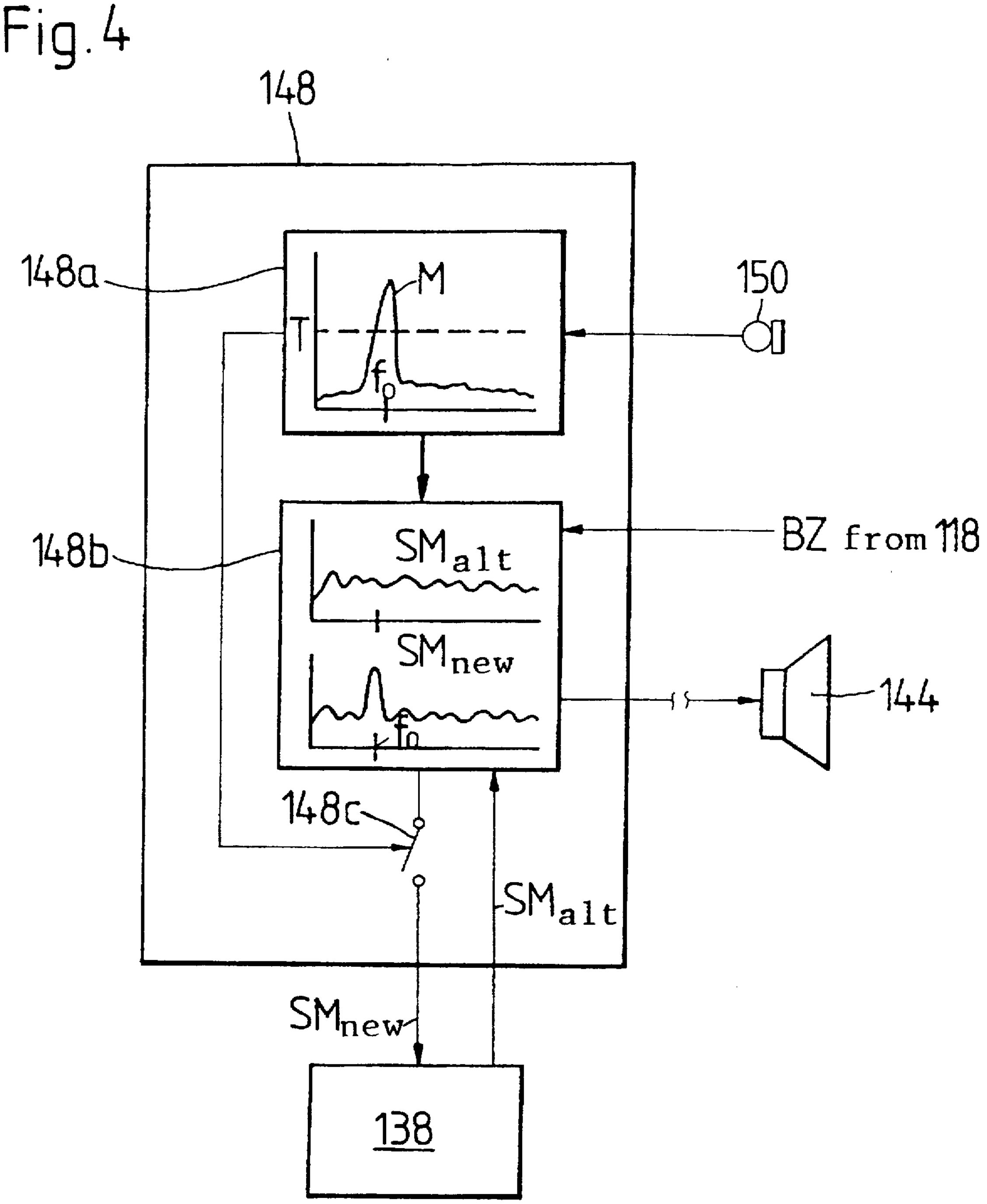
FIG. 4 is a schematic block diagram which explains the operation of the tuning device.

With reference to FIG. 4, the following description relates to the construction and function of the tuning device 148. A threshold value comparator 148a is supplied with an oscillation signal M by a microphone 150 which is located in the passenger compartment 112. The comparator 148a compares this oscillation signal M to a threshold value T which, in the illustrated example, has the same value for all frequencies f of the oscillation signal M. Basically, however, the threshold value T can also have any other frequency-dependent value. If the oscillation signal M exceeds the threshold value T at a defined oscillation frequency $f_0$, a corresponding detection signal is transmitted to an oscillation pattern modification device 148b, e.g., a synthesizer. The synthesizer 148b, as a function of the operating condition signal BZ fed to it by the operating condition determination device 118, has downloaded the corresponding oscillation pattern $SM_{old}$ from the memory device 138. It modifies this oscillation pattern $SM_{old}$ at the frequency $f_0$ determined by the comparator 148a to minimize the oscillation signal M detected by the microphone 150, and thereby generates a new oscillation pattern $SM_{new}$, which is transmitted to the loudspeaker 144 (by means of the selector apparatus 136, the tripping (or energizing) apparatus 139 and the output stage 142).

If the comparator 148a determines that the oscillation signal M picked up by the microphone 150 exceeds the threshold value T at no frequency, the comparator 148a gives a "save" command to a switch 148c, so that for the determined operating condition BZ, the adjusted oscillation pattern $SM_{new}$ is now stored in memory instead of the previously-stored oscillation pattern $SM_{old}$ in the memory device 138.

Although in the embodiment described above, the tuning device 148 performs the modification of the oscillation pattern stored in the memory device 138 as part of a control process, it is also possible to have the tuning device 148 contain fixed, specified oscillation patterns which have been determined on the basis of test vehicles under certain wear conditions. The tuning device 148 can then simply download those oscillation patterns which correspond to the current wear condition of the vehicle to which the tuning device has been connected into the memory device 138 on this vehicle 114. The wear condition can thereby be determined, for example, on the basis of the odometer reading.

Finally, it is basically also possible to leave the tuning device 148 continuously connected to the device 110.

Figure 5:
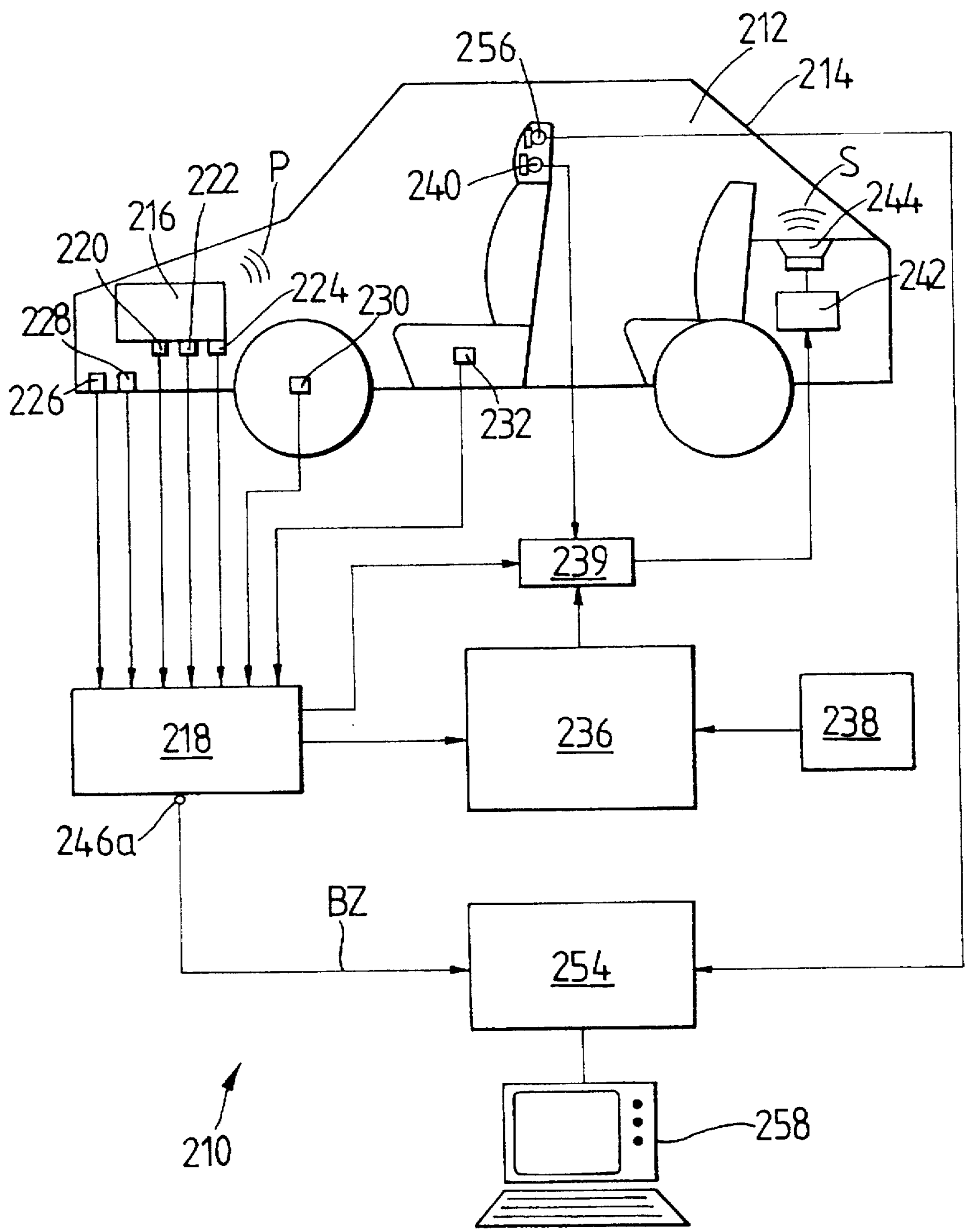
FIG. 5 is a schematic illustration similar to that of FIG. 1, in which the vehicle is also provided with an apparatus for the detection and analysis of defects.

FIG. 5 shows an additional embodiment in which the apparatus claimed by the present invention can be used for the detection and analysis of defects in the vehicle. The embodiment illustrated in FIG. 5 essentially corresponds to the embodiment illustrated in FIGS. 1 and 2. Therefore the analogous parts in FIG. 5 are identified by the same reference numbers as in FIGS. 1 and 2, but plus 200. The embodiment illustrated in FIG. 5 is described below only to the extent that it differs from the embodiment illustrated in FIG. 1, and reference is hereby expressly made to the description which accompanies FIG. 1.

The embodiment illustrated in FIG. 5 differs from the embodiment illustrated in FIG. 1 in particular because, in addition to the apparatus 210 to influence oscillations in the passenger compartment 212, there is also an apparatus 254 to detect and analyze defects of the vehicle 214. The apparatus 254 is connected on one hand by means of an interface 246a to the operating condition determination device 218, and on the other hand to a microphone 256 which is located in the passenger compartment 212. The microphone 256 measures a resultant oscillation in the passenger compartment 212 which results from a superimposition of the primary oscillation P caused by the noise source 216 and the secondary oscillation S emitted by the apparatus 210 via the loudspeaker 244. The apparatus 254, on the basis of the resultant signal picked up by the microphone 256, determines whether a defect exists, and if possible, identifies a correspondence between this defect and a defined component, under ideal conditions even identifying the type of defect of this component. The information indicated above it then displayed on a display apparatus 258.

Figure 6:
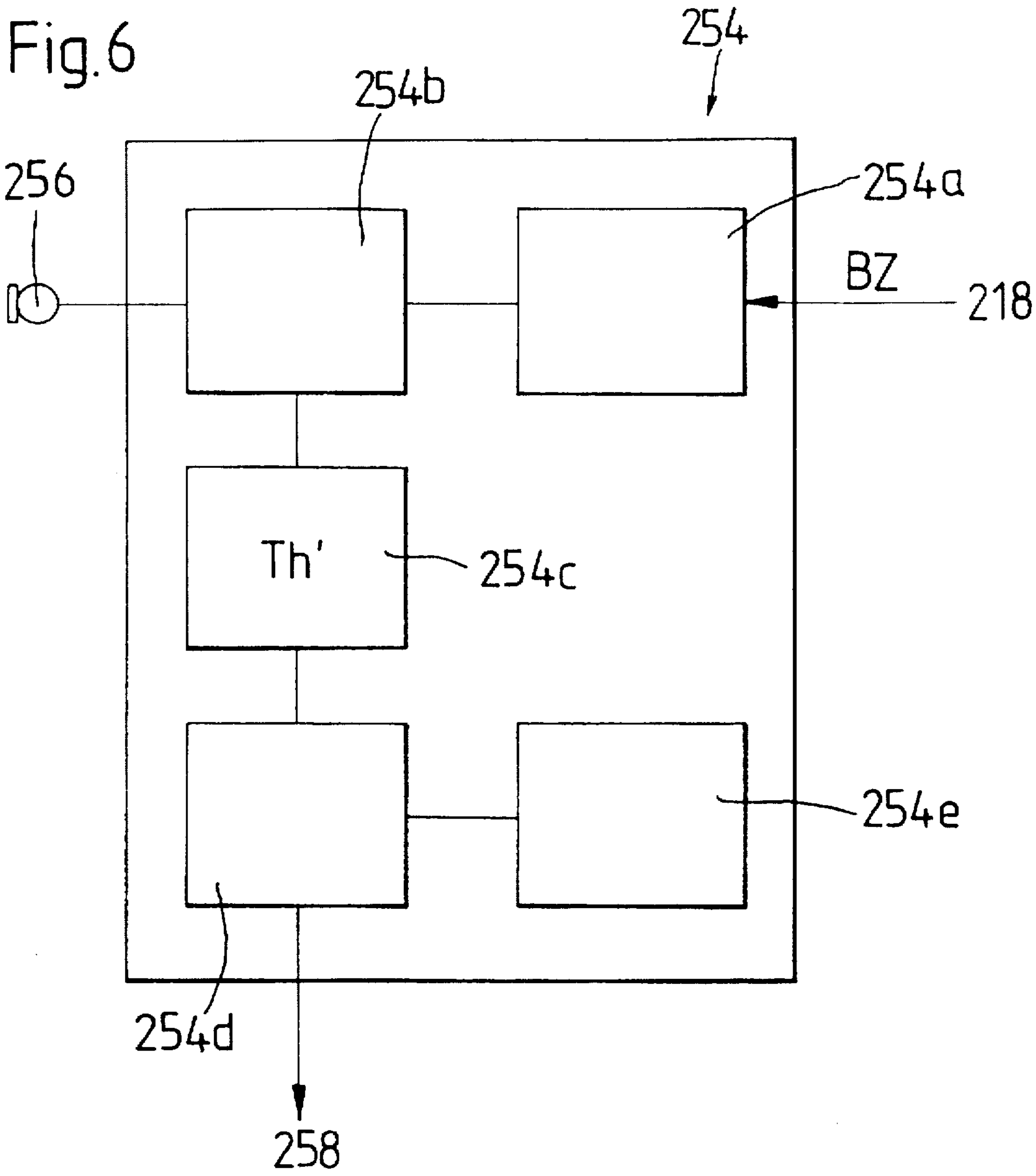
FIG. 6 is an illustration which explains the construction and the function of the apparatus for the detection and analysis of defects.

The defect detection and analysis device 254, as illustrated in FIG. 6, includes a memory device **254*a* which reads a corresponding oscillation pattern as a function of the operating condition BZ reported to it, and transmits it to a comparator device 254*b*. This comparator device 254*b* compares this oscillation pattern to the signal fed to it from the microphone 256, and transmits the resulting comparison signal to a filter device 254*c*. The filter device 254*c* allows only those components of the comparison signal indicating the deviations of the two oscillation patterns from one another to pass, the signal intensity of which exceeds a defined threshold value Th'. The resulting signal is transmitted to a diagnostic device 254*d* to analyze the potential defect. The result of the diagnosis is on one hand stored in an additional memory device 254*e* and on the other hand is displayed on the display device 258. If desired, the additional storage device 254*e*** also stores the signal which indicates the deviations of the two oscillation patterns from one another.

Figure 7:
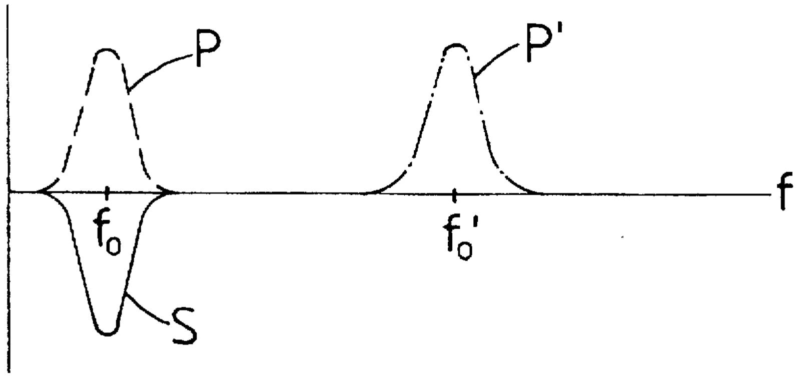
FIG. 7 is an illustration which explains the operation of the device for the detection and identification of defects illustrated in FIG. 5.

The following portion of the description refers to FIG. 7 and explains the method of operation of the diagnosis device **254*d* in greater detail. For this purpose, the source 216 of the noise is considered to be a single component, the noise from which is concentrated on account of resonance essentially around the natural frequency $f_0$ of this component. The spectrum of the non-defective component is indicated by the broken line P in FIG. 7. The secondary oscillation spectrum necessary to suppress this noise P is illustrated in FIG. 7** at S by the solid line. It is readily apparent that when these two spectra are superimposed, the result is destructive interference which leads to the extinction of the noise.

But if the component experiences a defect, e.g., if a tooth breaks in the transmission, the natural frequency of the component shifts and thus also the spectrum emitted by it. This displaced spectrum is illustrated by the dotted-dashed line at P' in FIG. 7. If the noise spectrum P' is superimposed on the secondary spectrum S, there is no destructive interference. Instead, the resultant spectrum contains two signal peaks, one of which occurs at the frequency $f_0'$ of the noise spectrum P' of the defective component, and the other of which occurs at the frequency $f_0$ of the secondary spectrum S, which in this case is no longer necessary. From the signal peak S, the diagnostic device **254*d* can determine the "non-defective" natural frequency $f_0$, and on the basis of this characteristic natural frequency, it can determine which component is defective. From the frequency difference between the "defective" natural frequency $f_0'$ of the defect spectrum P' and the above-referenced "non-defective" natural frequency $f_0$ of the component, with further knowledge of the instantaneous operating condition BZ of the vehicle 214**, conclusions can also be drawn concerning the type and severity of the defect.

The diagnosis device **254*d*, however, can also be used on a vehicle which is not equipped with an apparatus 210 to influence oscillations. In that case, the microphone 256 picks up the noise generated by the primary oscillations P in the passenger compartment 212. The diagnosis device 254*d* then compares the oscillation pattern of this noise with a secondary oscillation pattern S stored in it which corresponds to the current operating condition BZ of the vehicle 214, as described above with reference to FIG. 7. As mentioned above, the operating condition determination unit 18, or in this case 218**, is part of the sensor system which is conventionally present on a vehicle anyway.

Figure 8:
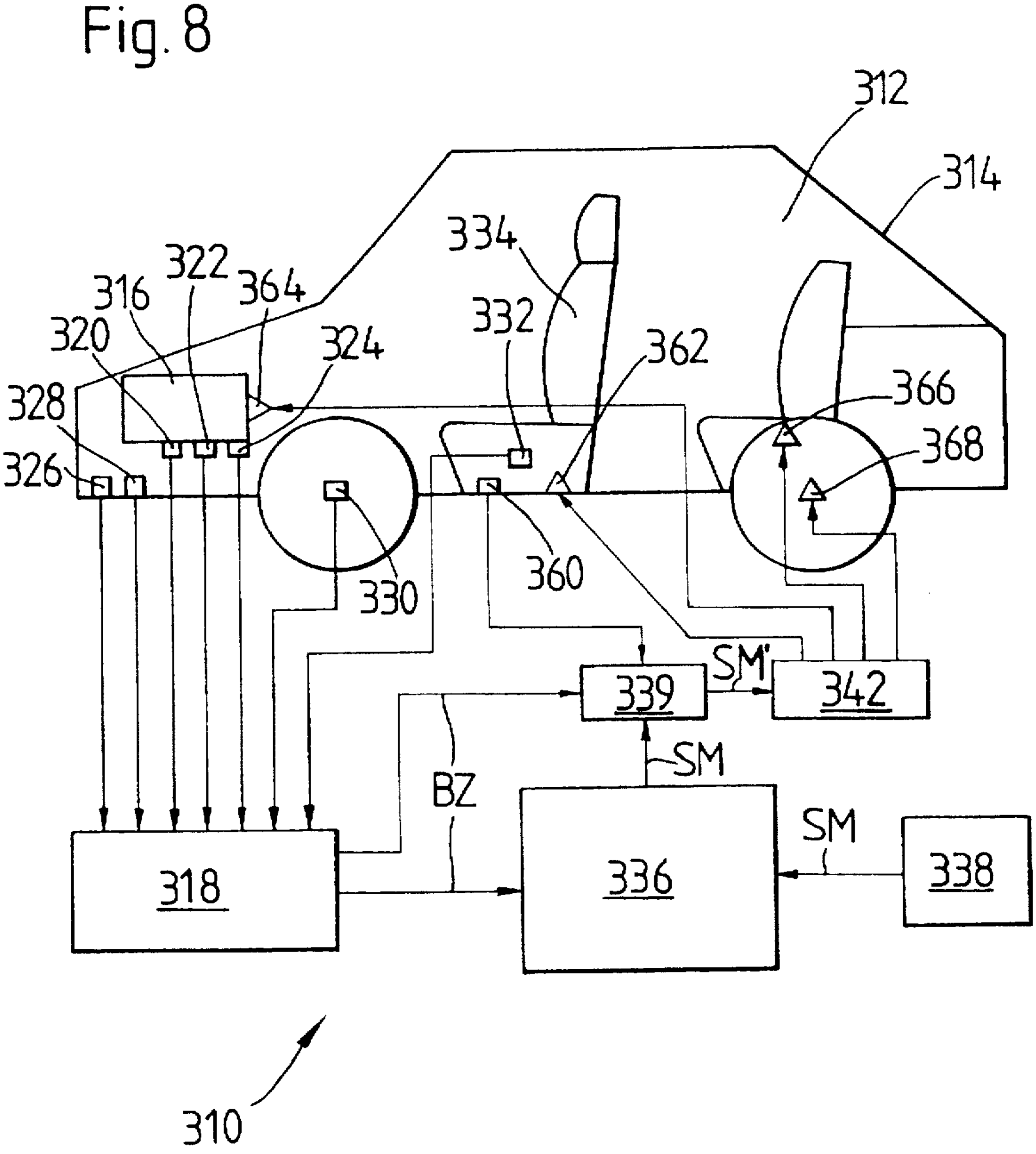
FIG. 8 illustrates a motor vehicle which is equipped with an apparatus to influence oscillations.

Although the apparatus claimed by the present invention has been explained above with reference to the example of influencing acoustical oscillations, it can also be used, as also mentioned several times above, with oscillations which are transmitted as physical vibrations via the body of the vehicle. FIG. 8 illustrates one embodiment for this application. The embodiment illustrated in FIG. 8 is essentially the same as the embodiment illustrated in FIG. 1. Therefore analogous parts are identified by the same reference numbers as in FIG. 1, but plus 300. The embodiment illustrated in FIG. 8 is described below only to the extent that it differs from the embodiment illustrated in FIG. 1, and reference is hereby expressly made to the description which accompanies FIG. 1.

The apparatus 310 which can be used to influence physical vibrations differs from the apparatus 10 which can be used to influence acoustical oscillations, in particular in that the tripping device 339 is connected to a vibration sensor 360 instead of a microphone (corresponding to the microphone 40). The determination of the phase angle by which the oscillation pattern SM stored in the memory device 338 must be shifted to suppress the primary vibrations emitted by the noise source 316 is made on the basis of the vibration signal measured by the vibration sensor 360 in the same manner as described above for the acoustical oscillation detected by the microphone 40. The phase-shifted vibration pattern SM' is emitted by means of an output stage 342 to one or more vibration generators. These vibration generators can be active seat bearings 362 for the seats 334 located in the passenger compartment 312, active transmission bearings 364, active differential bearings 366 and active axle bearings 368. The vibrations generated by these vibration generators 362–368 are superimposed on the vibrations emitted by the noise source 316 in the sense of suppressing the effects of these vibrations on the passengers seated in the passenger compartment 312. The vibration generators 362–368 are symbolized in FIG. 8 by triangles, so that they can be more easily distinguished from the sensors 320–332 and 360, which are symbolized by squares.

Basically, the apparatus 310 can also be used for the controlled generation of vibrations. For example, on a vehicle 314 equipped with an automatic transmission or a continuously shifting transmission, the "jerk" experienced by the driver or the passengers when the gears are shifted, which can be very slight or altogether absent, can be reinforced or simulated, so that such a transmission feels like the transmission to which the driver may be accustomed.

Some examples of speaker systems (e.g., loudspeaker systems) which may be utilized in conjunction with the present invention are to be found in U.S. Pat. No. 4,914,707; No. 5,129,004; No. 5,263,188; No. 5,297,212; No. 5,420,931; and No. 5,469,509, each of these issued U.S. patents being hereby expressly incorporated by reference herein.

Some examples of active noise cancellation systems utilizing electronic circuitry that may also be used in conjunction with the present invention are to be found in U.S. Pat. No. 5,347,586; No. 5,182,774; No. 5,222,148; No. 5,224,122; No. 5,226,016; No. 5,251,262; No. 5,359,662; No. 5,365,594; No. 5,432,857; No. 5,473,699; No. 5,473,702; and No. 5,388,080, each of these issued U.S. patents being hereby expressly incorporated herein.

Some examples of devices and methods for spectral analysis and comparison that may be used in conjunction with the present invention are to be found in U.S. Pat. No. 5,210,366; No. 5,308,773; No. 5,192,979; No. 5,224,036; No. 5,247,307; No. 5,179,571; and No. 5,192,979, each of these issued U.S. patents being hereby expressly incorporated by reference herein.

Some examples of envelope curve generators that may be utilized in conjunction with the present invention are to be found in U.S. Pat. No. 5,264,807 and No. 5,271,404, each of these issued U.S. patents being hereby expressly incorporated by reference herein.

Some examples of devices and methods relating to envelope families of curves that may be utilized in conjunction with the present invention are to be found in U.S. Pat. No. 5,365,238; No. 5,302,907 and No. 5,357,340, each of these issued U.S. patents being hereby expressly incorporated by reference herein.

Some examples of apparatuses and methods wherein frequency or spectral cover or overlap are discussed and/or employed and which may be used in conjunction with the present invention are to be found in U.S. Pat. No. 5,191,344; No. 5,294,402; No. 5,319,672; and No. 5,326,692, each of these issued U.S. patents being hereby expressly incorporated by reference herein.

One feature of the invention resides broadly in an apparatus 10 to influence oscillations in a passenger compartment 12 of a motor vehicle 14, comprising: a memory device 38 to store a plurality of predetermined oscillation patterns SM, an operating condition determination device 18 to determine the operating condition BZ of the motor vehicle 14, a selector device 36 to select an oscillation pattern SM from the plurality of stored oscillation patterns SM as a function of the operating condition BZ determined on the motor vehicle 14, and an oscillation generator device 39-42-44 to output oscillations corresponding to the selected oscillation pattern SM into the passenger compartment 12 of the motor vehicle 14.

Another feature of the invention resides broadly in the apparatus characterized by the fact that the oscillation generator device 39-42-44 corresponds to a tripping device 39 which, by transmitting a tripping signal to the oscillation generator device 39-42-44, causes the output of the oscillations S corresponding to the selected oscillation pattern SM in phase opposition to the primary oscillations P acting on the passenger compartment 12.

Yet another feature of the invention resides broadly in the apparatus characterized by the fact that the tripping device 39 comprises at least one oscillation sensor 40 which is located in the passenger compartment 12 to detect the oscillations in the passenger compartment 12 of the motor vehicle 14.

Still another feature of the invention resides broadly in the apparatus characterized by the fact that the tripping device 39 includes an envelope curve generator **39*a* to generate a predetermined envelope family of curves H which changes in its phase with regard to the primary oscillations P as a function of the operating condition BZ of the vehicle 14, as well as a tripping signal generator 39*b*** to output the tripping signal, when the envelope family of curves H has completely covered the primary oscillation P for a predetermined period of time.

A further feature of the invention resides broadly in the apparatus characterized by the fact that the operating condition determination device 18 comprises a speed sensor 20 to measure the speed of the engine 16 of the vehicle and/or a speed sensor 30 to measure the speed of the vehicle and/or a throttle valve sensor 22 to determine the degree of opening of a throttle valve of the engine of the vehicle and/or a gear sensor 24 to determine the currently-engaged gear of a transmission or the vehicle and/or at least one longitudinal acceleration sensor 26 to measure a longitudinal acceleration of the body of the vehicle and/or at least one lateral acceleration sensor 28 to measure a lateral acceleration of the body of the vehicle and/or at least one load sensor 32 to determine the load condition of the vehicle.

Another feature of the invention resides broadly in the apparatus characterized by the fact that it also comprises a monitoring device 33 to monitor its correct function, and if desired, a display device 35 which corresponds to the monitoring device 33 to display the abnormality detected, if any.

Yet another feature of the invention resides broadly in the apparatus characterized by the fact that it is realized with an interface **146*a*, 146*b*, 146*c* for a connection to a tuning device 148 to define the oscillation patterns SM to be stored in the memory device 138** as a function of specified operating conditions BZ of the vehicle.

Still another feature of the invention resides broadly in the apparatus characterized by the fact that the tuning device 148 comprises at least one oscillation sensor 15 located in the passenger compartment 112 to detect the resultant oscillation which results from the superimposition of the primary oscillation P and the secondary oscillation S corresponding to the oscillation pattern SM selected, as well as an optimization device **148*a*–148*b*** for the frequency-specific modification of the oscillation pattern.

A further feature of the invention resides broadly in the apparatus characterized by the fact that the optimization device **148*a*–148*b* comprises at least one comparator 148*a* which compares the amplitude of the resultant oscillation determined as a function of the oscillation frequency f with a threshold value T, which can be frequency-dependent if necessary, and emits a corresponding comparator signal to an oscillation pattern modification device 148*b*** which modifies the oscillation pattern SM to minimize the amplitude of the resultant oscillation determined, as a function of the comparator signal.

Another feature of the invention resides broadly in the apparatus characterized by the fact that the oscillations are acoustical oscillations, the oscillation generator device comprises at least one loudspeaker 44 located in the passenger compartment 12, and if necessary the oscillation sensors comprise microphones 40; 140, 150.

Yet another feature of the invention resides broadly in the apparatus characterized by the fact that the at least one loudspeaker 44 is part of an audio system, in particular a stereo system, present in the vehicle 14.

Still another feature of the invention resides broadly in the apparatus characterized by the fact that the microphones 40; 140, 150 are located in proximity to an area **34*b*** in which the passengers' ears are located when the vehicle is in motion.

A further feature of the invention resides broadly in the apparatus characterized by the fact that the oscillations are physical vibrations, the generator device comprises active bearings for the seats 334 in the passenger compartment 312 and/or active transmission bearings 364 and/or active differential bearings 366 and/or active axial bearings 368, and if necessary the oscillation sensors comprise vibration sensors 360.

Another feature of the invention resides broadly in the method to influence oscillations in a passenger compartment of a motor vehicle, comprising the following steps: determination of an operating condition BZ of the motor vehicle 14, selection of an oscillation pattern SM from a plurality of oscillation patterns stored in a memory device 38 as a function of the determined operating condition of the motor vehicle, and generation and output of the oscillations S corresponding to the selected oscillation pattern SM into the passenger compartment 12 of the motor vehicle 14.

Yet another feature of the invention resides broadly in the method characterized by the fact that the output into the passenger compartment 12 of the oscillations S corresponding to the selected oscillation pattern. SM is in phase opposition to the primary oscillations P acting on the passenger compartment 12.

Still another feature of the invention resides broadly in the method characterized by the fact that a predetermined envelope family of curves H, the phase of which changes with respect to the primary oscillations P is generated as a function of the operating condition BZ of the vehicle 14, and that the output of the oscillations S corresponding to the selected oscillation pattern is tripped in the passenger compartment 12 when the envelope family of curves H has completely covered the primary oscillation P for a specified length of time.

A further feature of the invention resides broadly in the method characterized by the fact that to determine the operating condition BZ, the speed of the engine 16 of the vehicle 14 and/or the speed of the vehicle 14 and/or the degree of opening of a throttle valve of the engine 16 of the 14 vehicle and/or the currently-engaged gear of the transmission of the vehicle 14 and/or a longitudinal acceleration of the body of the vehicle 14 and/or a lateral acceleration of the body of the vehicle 14 and/or a load condition of the vehicle 14 are determined.

Another feature of the invention resides broadly in the method characterized by the fact that the correct performance of the method is monitored by a monitoring device 33, and if desired, an abnormality identified during the monitoring is indicated to a user of the vehicle by a display unit 35.

Yet another feature of the invention resides broadly in the method characterized by the fact that oscillation patterns SM to be stored in the memory device 38 are defined as a function of predetermined operating conditions of the motor vehicle 14.

Still another feature of the invention resides broadly in the method characterized by the fact that resultant oscillations which result from the superimposition of the primary oscillations P and the oscillations S corresponding to the selected oscillation pattern SM are determined, and the oscillation pattern is modified in a frequency-specific manner to achieve a minimization of the amplitude of the resultant oscillations determined.

A further feature of the invention resides broadly in the method characterized by the fact that the amplitude of the resultant oscillation determined as a function of the oscillation frequency is compared to a threshold value T, which may be frequency-dependent if desired, and the oscillation pattern SM is modified to minimize the amplitude of the resultant oscillation determined as a function of the result of the comparison.

Another feature of the invention resides broadly in the method characterized by the fact that the oscillations are acoustical oscillations and the oscillations corresponding to the selected oscillation pattern SM are output by means of at least one loudspeaker 44 located in the passenger compartment 12, and if necessary the oscillations are detected and/or measured by means of microphones 40.

Yet another feature of the invention resides broadly in the method characterized by the fact that the oscillations are physical vibrations, and the oscillations corresponding to the selected oscillation pattern SM are output by means of active bearings 362 for the seats 334 located in the passenger compartment 312 and/or active transmission bearings 364 and/or active differential bearings 366 and/or active axle bearings 368, and if necessary, the oscillations are detected and/or measured by means of vibration sensors 360.

Still another feature of the invention resides broadly in the apparatus 254 to detect defects in a motor vehicle 214, comprising: a memory device 254*a*; 238 to store a plurality of predetermined oscillation patterns SM, an operating condition determination device 218 to determine an operating condition BZ of the motor vehicle 214, an oscillation sensor 256 to detect oscillations in a passenger compartment 212 of the motor vehicle 214, and a comparator device 254*b* to compare the oscillation pattern of the oscillations detected in the passenger compartment 212 to an oscillation pattern SM which corresponds to the determined operating condition BZ of the vehicle 214 and is stored in the memory device 254*a*; 238, and to output a signal which indicates the deviations of the two oscillation patterns from one another.

A further feature of the invention resides broadly in the apparatus characterized by the fact that the comparator device 254*b* comprises a filter device 254*c*, which lets pass only those components of the signal which indicates the deviations of the two oscillation patterns from one another, the signal strength of which exceeds a predetermined threshold value Th'.

Another feature of the invention resides broadly in the apparatus characterized by the fact that it comprises an additional memory device 254*e* to store the signal indicating the deviations of the two oscillation patterns from one another.

Yet another feature of the invention resides broadly in the apparatus characterized by the fact that it comprises a diagnostic device 254*d* to determine the type of defect occurring from the signal indicating the deviations of the two oscillation patterns from one another.

Still another feature of the invention resides broadly in the method to detect-defects on a motor vehicle 214, comprising the following steps: detection of oscillations in a passenger compartment 212 of the motor vehicle 214, comparison of the oscillation pattern of the oscillations detected in the passenger compartment 212 to an oscillation pattern SM corresponding to the determined operating condition of the motor vehicle 214 and stored in a memory device 254*a*; 238, and output of a signal which indicates the deviations of the two oscillation patterns from one another.

A further feature of the invention resides broadly in the method characterized by the fact that only those components of the signal indicating the deviations of the two oscillation patterns from one another are output, the signal strength of which exceeds a specified threshold Th'.

Another feature of the invention resides broadly in the method characterized by the fact that the signal indicating the deviations of the two oscillation patterns from one another is stored in an additional memory device 254*e*.

Yet another feature of the invention resides broadly in the method characterized by the fact that the type of defect which has occurred is determined from the signal indicating the deviations of the two oscillation patterns from one another.

The components disclosed in the various publications, disclosed or incorporated by reference herein, may be used in the embodiments of the present invention, as well as, equivalents thereof.

The appended drawings in their entirety, including all dimensions, proportions and/or shapes in at least one embodiment of the invention, are accurate and to scale and are hereby included by reference into this specification.

All, or substantially all, of the components and methods of the various embodiments may be used with at least one embodiment or all of the embodiments, if more than one embodiment is described herein.

All of the patents, patent applications and publications recited herein, and in the Declaration attached hereto, are hereby incorporated by reference as if set forth in their entirety herein.

The corresponding foreign patent publication applications, namely, Federal Republic of Germany Patent Application No. 195 31 402.6, filed on Aug. 26, 1995, having inventors Matthias Fischer, Reinhard Feldhaus, Andreas Orlamünder, and DE-OS 195 31 402.6 and DE-PS 195 31 402.6, as well as their published equivalents, and other equivalents or corresponding applications, if any, in corresponding cases in the Federal Republic of Germany and elsewhere, and the references cited in any of the documents cited herein, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents but also equivalent structures.

The invention as described hereinabove in the context of the preferred embodiments is not to be taken as limited to all of the provided details thereof, since modifications and variations thereof may be made without departing from the spirit and scope of the invention.

What is claimed is:

1. An apparatus for modifying noise oscillations transmitted to a passenger compartment of a vehicle, said noise oscillations being transmitted to said passenger compartment of said vehicle as a result of operation of said vehicle, said apparatus comprising:

memory means for storing a plurality of oscillation patterns;

operating condition determination means for determining at least one operating condition of said vehicle;

selector means for receiving said at least one operating condition from said operating condition determination means and for selecting an oscillation pattern from said plurality of oscillation patterns stored in said memory means based upon said at least one operating condition received from said operating condition determination means;

oscillation generation means for generating oscillations into said passenger compartment of said vehicle, said generated oscillations generated by said oscillation generation means corresponding to said selected oscillation pattern selected by said selector means from said plurality of oscillation patterns stored in said memory means;

said oscillation generation means comprising:

tripping means for generating a tripping signal; and oscillator means for receiving said tripping signal and for generating said oscillations in said passenger compartment of said vehicle which are substantially in phase opposition to said noise oscillations transmitted to said passenger compartment of said vehicle as said result of said operation of said vehicle;

said tripping means comprising oscillation sensor means for detecting oscillations in said passenger compartment of said vehicle;

said oscillation sensor means being disposed substantially within said passenger compartment of said vehicle;

said tripping means additionally comprising:

envelope curve generator means for generating an envelope family of curves;

said envelope family of curves generated by said envelope curve generator means changing in phase with regard to said noise oscillations as a function of said at least one operating condition of said vehicle; and tripping signal generator means for generating said tripping signal when said envelope family of curves substantially completely covers said noise oscillation for a determined period of time;

said vehicle comprises an engine for propelling said vehicle, a throttle for supplying fuel to said engine, and a transmission for transferring power from said engine;

said operating condition determination means comprising at least one of:

engine speed sensor means for measuring a speed of said engine;

vehicle speed sensor means for measuring a speed of said vehicle;

throttle valve sensor means for measuring a degree of opening of said throttle;

gear sensor means for determining a currently engaged gear of said transmission;

at least one longitudinal acceleration sensor means for determining a longitudinal acceleration of said vehicle;

at least one lateral acceleration sensor means for determining a lateral acceleration of said vehicle; and at least one load sensor for determining a load condition of said vehicle;

monitoring means for determining and monitoring the operation of said apparatus for modifying noise oscillation transmitted to said passenger compartment of said vehicle;

display means for generating a signal indicative of improper operation of said apparatus for modifying noise oscillation transmitted to said passenger compartment of said vehicle;

tuning means for generating at least some of said plurality of determined oscillation patterns;

interface means for connecting said tuning means to said memory means and for transferring said at least some of said plurality of determined oscillation patterns from said tuning means to said memory means;

said tuning means comprising:

additional oscillation sensor means being positioned in said passenger compartment of said vehicle;

said additional oscillation sensor means being for the detection of a resultant oscillation resulting from the superimposition of said noise oscillations and said oscillations generated in said passenger compartment of said vehicle by said oscillator means for a selected one of said plurality of determined oscillation patterns; and optimization means for the frequency-specific modification of said selected one of said plurality of oscillation pattern;

said optimization means comprising:

comparator means for comparing the amplitude of said resultant oscillation with a threshold value and for generating a comparator signal; and oscillation pattern modification means for modifying said selected one of said plurality of oscillation patterns to minimize the amplitude of said resultant oscillation.

2. An apparatus for modifying noise oscillations transmitted to a passenger compartment of a vehicle according to claim 1:

wherein said comparator means additionally comprises means for comparing said resultant oscillation at a plurality of oscillation frequencies with said threshold value, said threshold value having a magnitude varying with said oscillation frequency; and wherein said oscillation pattern modification means additionally comprises means for modifying said selected one of said plurality of oscillation patterns to minimize the amplitude of said resultant oscillation determined as a function of said comparator signal.

3. An apparatus for modifying noise oscillations transmitted to a passenger compartment of a vehicle according to claim 1:

wherein said oscillations generated in said passenger compartment by said oscillator means comprise acoustical oscillations;

wherein said oscillator means comprises at least one loudspeaker, said at least one loudspeaker being disposed within said passenger compartment of said vehicle; and wherein said oscillation sensor means comprises at least one microphone.

4. An apparatus for modifying noise oscillations transmitted to a passenger compartment of a vehicle according to claim 3:

wherein said vehicle comprises a vehicle audio system; and wherein said at least one loudspeaker comprises a portion of said vehicle audio system.

5. An apparatus for modifying noise oscillations transmitted to a passenger compartment of a vehicle according to claim 4:

wherein said vehicle includes a position for a passenger of said vehicle and a position for the ears of the passenger of said vehicle when said vehicle is in motion; and wherein said at least one microphone is disposed substantially adjacent said position for the ears of the passenger of said vehicle when said vehicle is in motion.

6. An apparatus for modifying noise oscillations transmitted to a passenger compartment of a vehicle according to claim 1:

wherein said vehicle comprises a vehicle seat for supporting a passenger of said vehicle, differential gearing means and at least one vehicle axle;

wherein said oscillations generated in said passenger compartment by said oscillator means comprises physical vibrations; and wherein said oscillator means comprises at least one of:

active bearing means for transmitting said physical vibrations to said vehicle seat;

active bearing means for transmitting said physical vibrations to said differential gearing means; and active bearing means for transmitting said physical vibrations to said at least one vehicle axle; and wherein said oscillation sensor means comprises at least one physical vibration sensor.

7. A method for modifying noise oscillations (P) transmitted to a passenger compartment of a vehicle, said noise oscillations (P) being transmitted to said passenger compartment of said vehicle as a result of operation of said vehicle, said method comprising the steps of:

providing memory means for storing a plurality of determined oscillation patterns;

determining an operating condition (BZ) of said vehicle;

selecting an oscillation pattern (SM) from said plurality of determined oscillation patterns stored in said memory means;

said selected oscillation pattern (SM) being selected from said plurality of determined oscillation patterns as a function of said determined operating condition (BZ) of said vehicle;

generating oscillations (S) into said passenger compartment of said vehicle;

said oscillations (S) generated into said passenger compartment of said vehicle corresponding to said selected oscillation pattern (SM);

said oscillations (S) generated into said passenger compartment of said vehicle corresponding to said selected oscillation pattern (SM) are in phase opposition to said noise oscillations (P) transmitted to said passenger compartment of said vehicle as said result of said operation of said vehicle;

generating an envelope family of curves (H) as a function of said determined operating condition (BZ) of said vehicle;

the phase of said generated envelope family of curves changing with respect to said noise oscillations (P);

tripping said output of said oscillations (S) corresponding to said selected oscillation pattern (SM) in said passenger compartment of said vehicle when said generated envelope family of curves (H) has substantially completely covered said noise oscillations (P) for a period of time;

said vehicle includes a vehicle body, an engine, a throttle for supplying said engine with fuel, and a transmission for transferring power from said engine;

said determined operating condition (BZ) of said vehicle comprises at least one of:

a speed of said engine;

a speed of said vehicle;

a degree of opening of said throttle;

a currently engaged gear of said transmission;

a longitudinal acceleration of said vehicle body;

a lateral acceleration of said vehicle body; and a load condition of said vehicle;

providing monitoring means for monitoring the operation of said method for modifying noise oscillations transmitted to said passenger compartment of said vehicle and for generating a signal indicating improper operation of said method;

operating said monitoring means to thereby provide to an operator of said vehicle said signal indicating improper operation of said method;

defining said plurality of oscillation patterns stored in said memory means as a function of a plurality of determined operating conditions of said vehicle;

superimposing at least:

said noise oscillations (P); and said oscillations (S) generated into said passenger compartment of said vehicle and corresponding to said selected oscillation pattern (SM);

forming a resultant oscillation from said superimposition of said noise oscillations (P) and said oscillations (S) generated into said passenger compartment of said vehicle;

modifying said selected oscillation pattern (SM) to substantially minimize the amplitude of said resultant oscillation;

said selected oscillation pattern (SM) being modified over a plurality of frequencies of said selected oscillation pattern (SM);

comparing the amplitude of said resultant oscillation to a threshold value (T); and modifying said selected oscillation pattern (SM) to substantially minimize said amplitude of said resultant oscillation.

8. A method for modifying noise oscillations transmitted to a passenger compartment of a vehicle according to claim 7, said method additionally comprising the further steps of:

comparing said resultant oscillation at a plurality of oscillation frequencies with said threshold value, said threshold value having a magnitude varying with said oscillation frequency; and modifying said selected one of said plurality of oscillation patterns to minimize the amplitude of said resultant oscillation determined as a function of said comparator signal.

9. A method for modifying noise oscillations transmitted to a passenger compartment of a vehicle according to claim 7:

wherein said oscillations (S) generated into said passenger compartment of said vehicle comprise acoustical oscillations;

wherein said step of generating said oscillations (S) into said passenger compartment of said vehicle comprises the steps of:

providing at least one loudspeaker disposed within said passenger compartment of said vehicle;

generating said oscillations (S) into said passenger compartment of said vehicle through said at least one loudspeaker;

providing at least one microphone disposed within said passenger compartment of said vehicle; and detecting said resultant oscillation through said at least one microphone.

10. A method for modifying noise oscillations transmitted to a passenger compartment of a vehicle according to claim 7:

wherein said vehicle includes at least one passenger seat disposed in said passenger compartment of said vehicle, transmission means, differential means and an axle;

wherein said oscillations (S) generated into said passenger compartment of said vehicle comprise physical vibrations;

wherein said oscillations' (S) generated into said passenger compartment of said vehicle and corresponding to said selected oscillation pattern (SM) are generated through at least one of:

active bearing means disposed in said at least one passenger seat;

active bearing means disposed in said transmission means;

active bearing means disposed said differential means; and active bearing means disposed in said axle; and wherein said method comprises the additional steps of:

disposing at least one physical vibration sensor in said passenger compartment of said vehicle; and detecting said resultant oscillations through said at least one physical vibration sensor.

11. An apparatus for modifying noise oscillations transmitted to a passenger compartment of a vehicle, said noise oscillations being transmitted to said passenger compartment of said vehicle as a result of operation of said vehicle, said apparatus comprising:

memory means for storing a plurality of oscillation patterns;

first sensor means for determining at least one operating condition of said vehicle;

selector means for receiving said at least one operating condition from said first sensor means and for selecting an oscillation pattern from said plurality of oscillation patterns stored in said memory means based upon said at least one operating condition received from said first sensor means;

oscillation generation means for generating oscillations into said passenger compartment of said vehicle, said generated oscillations generated by said oscillation generation means corresponding to said selected oscillation pattern selected by said selector means from said plurality of oscillation patterns stored in said memory means;

second sensor means being positioned in said passenger compartment of said vehicle;

said second sensor means being for the detection of a resultant oscillation resulting from a superimposition of said noise oscillations and said oscillations generated in said passenger compartment of said vehicle by said oscillation generation means for a selected one of said plurality of determined oscillation patterns; and oscillation pattern modification means for modifying said selected one of said plurality of oscillation patterns to minimize the amplitude of said resultant oscillation.

12. The apparatus for modifying noise oscillations transmitted to a passenger compartment of a vehicle according to claim 11, said apparatus comprising:

tuning means for generating at least some of said plurality of oscillation patterns; and interface means for connecting said tuning means to said memory means and for transferring said at least some of said plurality of oscillation patterns from said tuning means to said memory means.

13. The apparatus for modifying noise oscillations transmitted to a passenger compartment of a vehicle according to claim 12, wherein said oscillation pattern modification means comprises:

comparator means for comparing the amplitude of said resultant oscillation with a threshold value and for generating a comparator signal; and means for modifying said selected one of said plurality of oscillation patterns to minimize the amplitude of said resultant oscillation in response to said comparator signal.

14. The apparatus for modifying noise oscillations transmitted to a passenger compartment of a vehicle according to claim 13, wherein:

said oscillation generation means comprises:

tripping means for generating a tripping signal; and oscillator means for receiving said tripping signal and for generating said oscillations in said passenger compartment of said vehicle which are substantially in phase opposition to said noise oscillations transmitted to said passenger compartment of said vehicle as said result of said operation of said vehicle.

15. The apparatus for modifying noise oscillations transmitted to a passenger compartment of a vehicle according to claim 14, wherein:

said tripping means comprises oscillation sensor means for detecting oscillations in said passenger compartment of said vehicle; and said oscillation sensor means being disposed substantially within said passenger compartment of said vehicle.

16. The apparatus for modifying noise oscillations transmitted to a passenger compartment of a vehicle according to claim 15, wherein said tripping means additionally comprises:

envelope curve generator means for generating an envelope family of curves changing in phase with regard to said noise oscillations as a function of said at least one operating condition of said vehicle; and tripping signal generator means for generating said tripping signal when said envelope family of curves substantially completely covers said noise oscillation for a determined period of time.

17. The apparatus for modifying noise oscillations transmitted to a passenger compartment of a vehicle according to claim 16, wherein:

said vehicle comprises an engine for propelling said vehicle, a throttle for supplying fuel to said engine, and a transmission for transferring power from said engine; and said first sensor means comprises at least one of:

engine speed sensor means for measuring a speed of said engine;

vehicle speed sensor means for measuring a speed of said vehicle;

throttle valve sensor means for measuring a degree of opening of said throttle;

gear sensor means for determining a currently engaged gear of said transmission;

at least one longitudinal acceleration sensor means for determining a longitudinal acceleration of said vehicle;

at least one lateral acceleration sensor means for determining a lateral acceleration of said vehicle; and at least one load sensor for determining a load condition of said vehicle.

18. The apparatus for modifying noise oscillations transmitted to a passenger compartment of a vehicle according to claim 17, said apparatus comprising:

monitoring means for determining and monitoring the operation of said apparatus for modifying noise oscillation transmitted to said passenger compartment of said vehicle; and display means for generating a signal indicative of improper operation of said apparatus for modifying noise oscillation transmitted to said passenger compartment of said vehicle.

19. The apparatus for modifying noise oscillations transmitted to a passenger compartment of a vehicle according to claim 18, wherein:

said vehicle comprises a vehicle seat for supporting a passenger of said vehicle, differential gearing means and at least one vehicle axle;

said oscillator means for generating oscillations in said passenger compartment comprises means for generating physical vibrations; and said oscillator means comprises at least one of:

active bearing means for transmitting said physical vibrations to said vehicle seat;

active bearing means for transmitting said physical vibrations to said differential gearing means; and active bearing means for transmitting said physical vibrations to said at least one vehicle axle; and said oscillation sensor means comprises at least one physical vibration sensor.

20. The apparatus for modifying noise oscillations transmitted to a passenger compartment of a vehicle according to claim 18, wherein:

said comparator means additionally comprises means for comparing said resultant oscillation at a plurality of oscillation frequencies with said threshold value; and said threshold value having a magnitude varying with said oscillation frequency.

21. The apparatus for modifying noise oscillations transmitted to a passenger compartment of a vehicle according to claim 20, wherein:

said oscillator means for generating oscillations in said passenger compartment comprises means for generating acoustical oscillations;

said oscillator means comprises at least one loudspeaker;

said at least one loudspeaker being disposed within said passenger compartment of said vehicle; and said oscillation sensor means comprises at least one microphone.

22. The apparatus for modifying noise oscillations transmitted to a passenger compartment of a vehicle according to claim 21, wherein:

said vehicle comprises a vehicle audio system; and said at least one loudspeaker comprises a portion of said vehicle audio system.

23. The apparatus for modifying noise oscillations transmitted to a passenger compartment of a vehicle according to claim 22, wherein:

said vehicle includes a position for a passenger of said vehicle and a position for the ears of the passenger of said vehicle when said vehicle is in motion; and said at least one microphone is disposed substantially adjacent to said position for the ears of the passenger of said vehicle when said vehicle is in motion.

24. A method for modifying noise oscillations transmitted to a passenger compartment of a vehicle, said noise oscillations being transmitted to said passenger compartment of said vehicle as a result of operation of said vehicle, said method comprising the steps of:

providing memory means for storing a plurality of determined oscillation patterns;

determining an operating condition of said vehicle;

selecting an oscillation pattern from said plurality of determined oscillation patterns stored in said memory means;

said selected oscillation pattern being selected from said plurality of determined oscillation patterns as a function of said determined operating condition of said vehicle;

generating oscillations into said passenger compartment of said vehicle;

said oscillations generated into said passenger compartment of said vehicle corresponding to said selected oscillation pattern;

superimposing at least:

said noise oscillations; and said oscillations generated into said passenger compartment of said vehicle and corresponding to said selected oscillation pattern;

forming a resultant oscillation from said superimposition of said noise oscillations and said oscillations generated into said passenger compartment of said vehicle; and modifying said selected oscillation pattern to substantially minimize the amplitude of said resultant oscillation.

25. The method for modifying noise oscillations transmitted to a passenger compartment of a vehicle according to claim 24, said method additionally comprising the steps of:

comparing the amplitude of said resultant oscillation to a threshold value; and modifying said selected oscillation pattern to substantially minimize said amplitude of said resultant oscillation.

26. The method for modifying noise oscillations transmitted to a passenger compartment of a vehicle according to claim 25, said method comprises the additional steps of:

generating an envelope family of curves as a function of said determined operating condition of said vehicle;

changing the phase of said generated envelope family of curves with respect to said noise oscillations; and tripping an output of said oscillations corresponding to said selected oscillation pattern in said passenger compartment of said vehicle when said generated envelope family of curves has substantially completely covered said noise oscillations for a period of time.

27. The method for modifying noise oscillations transmitted to a passenger compartment of a vehicle according to claim 26, wherein:

said step of generating oscillations into said passenger compartment of said vehicle comprises generating oscillations in phase opposition to said noise oscillations transmitted to said passenger compartment of said vehicle as said result of said operation of said vehicle.

28. The method for modifying noise oscillations transmitted to a passenger compartment of a vehicle according to claim 27, wherein:

said vehicle includes a vehicle body, an engine, a throttle for supplying said engine with fuel, and a transmission for transferring power from said engine; and said step of determining an operating condition of said vehicle comprises determining at least one of:

a speed of said engine;

a speed of said vehicle;

a degree of opening of said throttle;

a currently engaged gear of said transmission;

a longitudinal acceleration of said vehicle body;

a lateral acceleration of said vehicle body; and a load condition of said vehicle.

29. The method for modifying noise oscillations transmitted to a passenger compartment of a vehicle according to claim 28, said method comprises the additional steps of:

providing monitoring means for monitoring the operation of said method for modifying noise oscillations transmitted to said passenger compartment of said vehicle and for generating a signal indicating improper operation of said method; and operating said monitoring means to thereby provide to an operator of said vehicle said signal indicating improper operation of said method.

30. The method for modifying noise oscillations transmitted to a passenger compartment of a vehicle according to claim 29, said method comprises the additional step of defining said plurality of oscillation patterns stored in said memory means as a function of a plurality of determined operating conditions of said vehicle.

31. The method for modifying noise oscillations transmitted to a passenger compartment of a vehicle according to claim 30, said method additionally comprising the steps of:

comparing said resultant oscillation at a plurality of oscillation frequencies with said threshold value, said threshold value having a magnitude varying with said oscillation frequency;

modifying said selected one of said plurality of oscillation patterns to minimize the amplitude of said resultant oscillation determined as a function of said comparator signal; and modifying said selected oscillation pattern over a plurality of frequencies of said selected oscillation pattern.

32. The method for modifying noise oscillations transmitted to a passenger compartment of a vehicle according to claim 31, wherein:

said vehicle includes at least one passenger seat disposed in said passenger compartment of said vehicle, transmission means, differential means and an axle;

said oscillations generated into said passenger compartment of said vehicle comprise physical vibrations;

said step of generating said oscillations into said passenger compartment of said vehicle comprises generating said oscillations through at least one of:

active bearing means disposed in said at least one passenger seat;

active bearing means disposed in said transmission means;

active bearing means disposed said differential means; and active bearing means disposed in said axle;

said method comprises the additional steps of:

disposing at least one physical vibration sensor in said passenger compartment of said vehicle; and detecting said resultant oscillations through said at least one physical vibration sensor.

33. The method for modifying noise oscillations transmitted to a passenger compartment of a vehicle according to claim 31, wherein:

said oscillations generated into said passenger compartment of said vehicle comprise acoustical oscillations;

said step of generating said oscillations into said passenger compartment of said vehicle comprises the steps of:

providing at least one loudspeaker disposed within said passenger compartment of said vehicle;

generating said oscillations into said passenger compartment of said vehicle through said at least one loudspeaker;

providing at least one microphone disposed within said passenger compartment of said vehicle; and detecting said resultant oscillation through said at least one microphone.

* * * * *